United States Patent
Saito et al.

(10) Patent No.: US 7,492,970 B2
(45) Date of Patent: Feb. 17, 2009

(54) REPORTING SYSTEM IN A NETWORKED ENVIRONMENT

(75) Inventors: Motoaki Saito, Tokyo (JP); Kazuo Takahashi, Tokyo (JP)

(73) Assignee: TeraRecon, Inc., San Mateo, CA (US)

(*) Notice: Subject to any disclaimer, the term of this patent is extended or adjusted under 35 U.S.C. 154(b) by 725 days.

(21) Appl. No.: 10/845,552

(22) Filed: May 12, 2004

(65) Prior Publication Data
US 2005/0254729 A1 Nov. 17, 2005

(51) Int. Cl.
G06K 9/54 (2006.01)
G06K 9/60 (2006.01)
G06K 9/00 (2006.01)
G06K 9/36 (2006.01)
G06K 9/40 (2006.01)
G06K 9/38 (2006.01)

(52) U.S. Cl. .............. 382/305; 382/128; 382/132; 382/232; 382/254

(58) Field of Classification Search ............... 382/128, 382/305
See application file for complete search history.

(56) References Cited

U.S. PATENT DOCUMENTS

| | | | | |
|---|---|---|---|---|
| 5,724,580 A | * | 3/1998 | Levin et al. | 707/104.1 |
| 5,807,256 A | * | 9/1998 | Taguchi et al. | 600/425 |
| 6,216,104 B1 | | 4/2001 | Moshfeghi et al. | |
| 6,551,243 B2 | * | 4/2003 | Bocionek et al. | 600/300 |
| 6,556,724 B1 | * | 4/2003 | Chang et al. | 382/299 |
| 6,574,629 B1 | * | 6/2003 | Cooke et al. | 707/10 |
| 6,621,918 B1 | * | 9/2003 | Hu et al. | 382/128 |
| 6,766,297 B1 | * | 7/2004 | Lamer et al. | 704/270 |
| 6,819,785 B1 | * | 11/2004 | Vining et al. | 382/128 |
| 7,209,578 B2 | * | 4/2007 | Saito et al. | 382/128 |
| 2003/0156745 A1 | | 8/2003 | Saito et al. | |
| 2007/0192138 A1 | | 8/2007 | Saito et al. | |

FOREIGN PATENT DOCUMENTS

| | | | |
|---|---|---|---|
| JP | 2003-085284 | | 3/2003 |
| JP | 2003085284 A | * | 3/2003 |
| JP | 2001000017 | | 5/2003 |
| JP | 2003-00025 | | 7/2003 |
| JP | 2005-044321 | | 2/2005 |

OTHER PUBLICATIONS

Machine Translation on JP2003-85284.*
Patent Abstract for Japan 2001-373389, filed Feb. 11, 2001, published May 13, 2003, 2 pages.
Meyer-Ebrecht, D., "The Filmless' Radiology Department—A Challenge for the Introduction of Image Processing into the Medical Routine Work," IEEE, Apr. 1992, pp. 13-20.

* cited by examiner

*Primary Examiner*—Jingge Wu
*Assistant Examiner*—Jose M Torres
(74) *Attorney, Agent, or Firm*—Blakely, Sokoloff, Taylor & Zafman LLP (57) ABSTRACT

A system is provided wherein data processing devices are connected to a high-speed picture archiving and communications system (PACS) server network that archives and transmits medical image data. As part of a diagnostic process, medical images are processed at the data processing devices and image processing parameter (IPP) sets are created. The image processing parameters are attached to image diagnosis reports and can be used to recreate the processing of key images that are referenced in the image diagnosis reports. Users of the diagnostic reports can send the IPP sets to the PACS server network to recreate and retrieve key diagnostic images. The image data can be compressed for transmission over low bandwidth networks.

26 Claims, 5 Drawing Sheets

REPORTING SYSTEM IN A NETWORKED ENVIRONMENT

FIELD OF THE INVENTION

This invention relates to a system for the utilization of medical data and for the preparation of reports with images for medical purposes in a networked environment.

BACKGROUND OF THE INVENTION

Images that are used for medical purposes are created by medical imaging devices such as X-ray machines, X-ray computer tomography (CT) machines or magnetic resonance imaging (MRI) machines in the image diagnostic facilities of medical institutions. The images are used by diagnostic specialists, in the course of diagnostic image analysis, who use image-processing systems to manipulate and interpret the medical images. The results of a diagnosis of such images are described in image diagnosis reports that are sent to departments that request these reports.

Conventional systems make it possible to capture unprocessed digital images on image servers so that image examinations can be distributed to image display devices via a network on demand, and then introduced into a PACS (picture archiving and communication system) for storage and retrieval of the images.

In the past, the results of a diagnosis of the images were manually copied into an image diagnostic report and the report was then distributed to requesting departments. The image information forming the basis of the image diagnosis was furnished to requesting departments by the diagnostician in the form of a handwritten sketch called a schema as a part of the written report.

More recently, hospital information systems have used word processors to create and transmit image diagnosis reports both for archiving purposes and for distribution to departments that request the reports. The image diagnosis reports are stored in an electronic file and they are either sent to a terminal computer at the requesting department, or transmitted with e-mail. In order to reduce the amount of data transmitted and stored throughout a network, the image data forming the basis of the image diagnosis is scaled down to reduce the size and the resolution of the images before it is transmitted to requesting departments. Therefore, the reports contain much less diagnostic image information than the original images.

For example, a single two-dimensional imaging examination with a CT scanner may produce several hundred pages of image data, each page having 512×512 pixels with a pixel depth of 16 bits. However, the image diagnosis report may have only 1 or 2 pages of images with a resolution of 256×256 pixels and a pixel depth of only 8 bits.

The advent of three-dimensional imaging and four-dimensional imaging (three spatial dimensions plus time) technology has exacerbated the problem because the image files are much larger than 2D files. Moreover, it is more important to maintain the resolution of the 3D and 4D files because they are used in ways that require great precision, such as design and control of surgical procedures and the fabrication of prosthetics and implants for plastic surgery. One advantage of 3D and 4D images in a diagnostic setting is that they can be manipulated and viewed from different angles. While it is relatively easy to create and manipulate these images in imaging departments having specialized equipment, it is difficult to create and reproduce the images in the using departments, because very large amounts of data must be transmitted through the user network. In many cases, the network that connects the user community (e.g., doctors, wards, operating theatres, etc.) to the imaging department is a narrow bandwidth network that cannot support the required data rates in real time. Furthermore, information flow and control is typically only one way. That is, the image diagnostic reports are created and distributed to using departments, but users cannot modify the images or interactively access additional information. In a large medical facility, there my be hundreds or even thousands of terminals connected to the user network, so it is not feasible to upgrade the network and terminals for high-speed operation.

Figure 1:
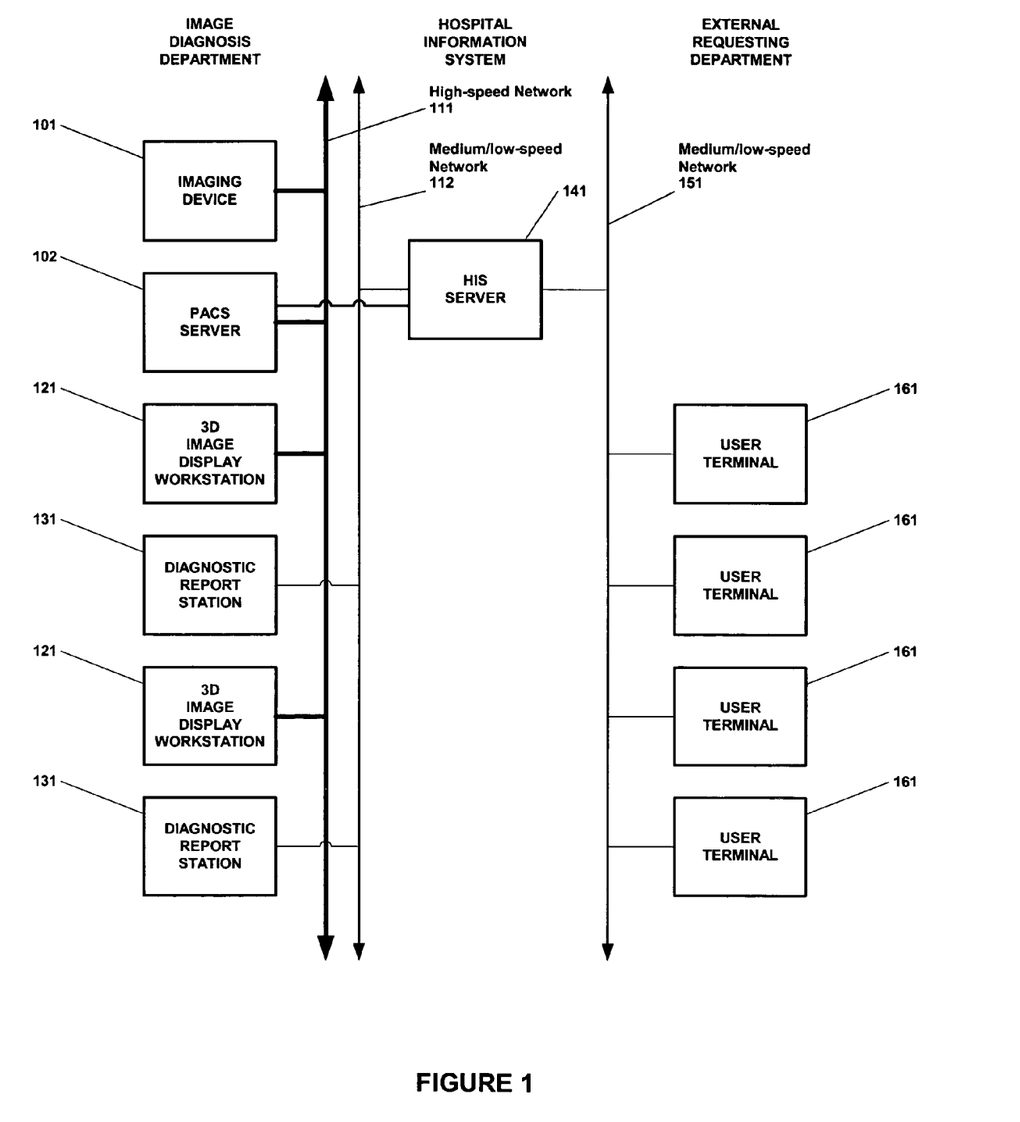
FIG. 1 is a block diagram of a conventional system configuration used to create and disseminate diagnostic reports with medical images in a network environment.

FIG. 1 is a block diagram illustrating a conventional system of a network environment of image diagnosis devices for an image diagnosis department and requesting departments. An X-ray CT scanner 101, which is one example of an imaging device, creates unprocessed 2D image data which is stored on a PACS server 102. Image display workstations 121 receive stored image data from the PACS server via network 111. The workstations 121 are optimized for processing the 2D images created by the imaging device 101, and produce enhanced 2D images as well as 3D and 4D images which are stored on the PACS server. The network 111 is a large-capacity, high-speed network. Diagnostic specialists perform medical diagnoses at the workstations 121 by processing the image data received from the PACS server 102.

Diagnostic report stations 131 are used by the diagnostic specialists to create image diagnosis reports. An image diagnosis specialist observes two-dimensional images by using image display workstations 121, creates and observes diagnostic images, and creates image diagnosis reports based on the findings obtained in this manner. The diagnostic images, which are very large data files, are stored on the PACS server. As previously mentioned, the network connecting the image diagnosis department with the requesting departments typically has a narrow bandwidth, so the diagnostic images which are attached to the reports are low resolution versions of the images stored on the PACS server.

A hospital information system (HIS) server 141 archives the diagnostic reports and attached low resolution images, and distributes the reports and images to requesting departments. A network 151 is used to distribute reports to user terminals 161 in the requesting departments from the HIS server 141. The users in the requesting departments use the user terminals 161 to view the image diagnosis reports and observe the low-resolution images attached to these reports.

As a result, the value of the diagnostic reports is reduced because the low-resolution images attached to the diagnostic reports provide much less information than the original high-resolution images. At the same time, the high-resolution images consume a large amount of storage space on the PACS server. Therefore, it is desirable to have a system that is capable of providing medical diagnostic reports with high-resolution diagnostic images, to users on low bandwidth networks. It is also desirable to have a system that is capable of providing such high-resolution images without consuming such large amounts of storage space on the image server.

SUMMARY OF THE INVENTION

A system and method for archiving, processing and analyzing image data in a networked environment is disclosed. In certain embodiments, unprocessed image data is obtained from imaging devices and is stored in an image archive for subsequent retrieval, processing and analysis. The unprocessed images are processed in an image processor to create processed images that are subsequently analyzed. The sequence of image processing operations is recorded as a sequence of image processing parameters that are stored in a data file with an image analysis report.

The image analysis reports may be distributed to terminal devices on a network where the reports may be read by users. The users may view the processed images by sending the image processing parameters corresponding to the desired image processor. At the image processor, the image processing parameters may be used to specify and transfer the unprocessed image data from the image archive to the image processor where the original sequence of image processing operations is repeated to reconstruct the processed image. The reconstructed image may then be transmitted to the user at the terminal device over the network. The image may be compressed to conserve bandwidth.

Other features of the present invention will be apparent from the accompanying drawings and from the detailed description that follows.

BRIEF DESCRIPTION OF THE DRAWINGS

The present invention is illustrated by way of example and not limitation in the figures of the accompanying drawings, in which like references indicate like elements and in which.

DETAILED DESCRIPTION

The following is a description of a report creating system for medical images in a network environment and a system using medical image data and medical information data.

Figure 2:
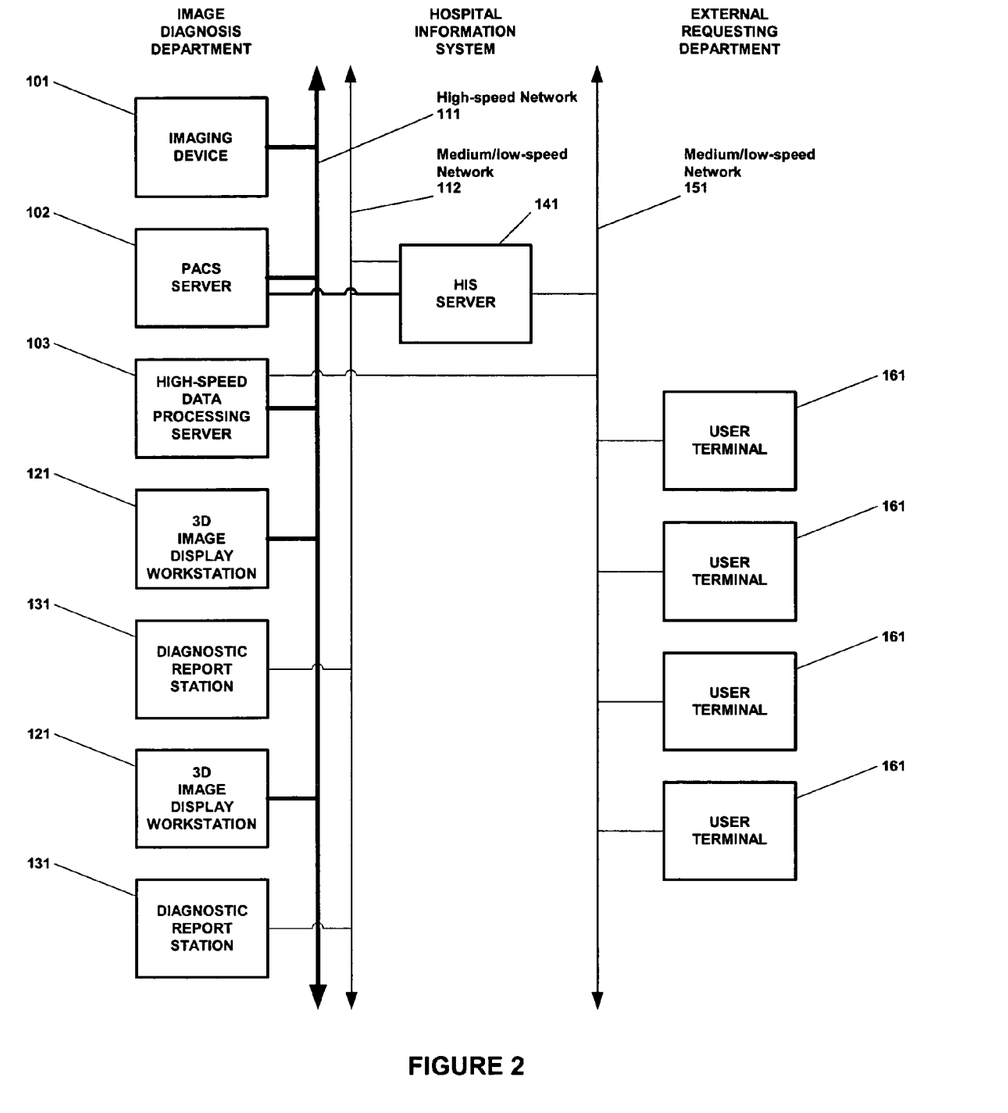
FIG. 2 is a block diagram of a system to create and disseminate diagnostic reports with medical images and other medical information in a network environment according to an embodiment of the invention.

FIG. 2 is a block diagram showing a network environment of a system according to one embodiment of the invention. An imaging device 101, which may be an X-ray CT scanner, a magnetic resonance imaging scanner, an ultrasound scanner or any other imaging device, generates unprocessed image data which contains a plurality of profiles of the object scanned by the imaging device 101. The unprocessed image data is transmitted on a high-speed, high capacity network 111 and is stored on a Picture Archiving And Communications System (PACS) server 102. Unprocessed image data stored on the PACS server 102 is acquired over the high-speed network 111 by an image display workstation 121.

In one embodiment of the invention, image display workstations 121, operated by a diagnostic specialist, use image-processing hardware and software to create diagnostic images from the unprocessed image data. The diagnostic images may be two-dimensional, three-dimensional or four-dimensional images, a four dimensional image being a series of three-dimensional images in time. The software that controls the image-processing process also generates Image-Processing Parameter (IPP) sets for each diagnostic image that is created. Each IPP set includes parameters that specify the unprocessed image data that forms the basis of the image-processed diagnostic image, as well as the image-processing steps that were used to create the diagnostic image and the image display parameters.

Reporting stations 131 are report creating terminals, which may be co-located with the image display workstations, that are used by the diagnostic specialist to create image diagnosis reports based on the findings from the diagnostic images developed on the image display workstation 121. In the course of writing the diagnostic report, the diagnostic specialist will typically select a number of key images to support the diagnosis. That is, from the perhaps many image-processed images that are created and viewed by the diagnostic specialist, a particular subset of images will be considered key images that are essential to the diagnosis. The IPP sets associated with these key images are known as key IPP sets. When the diagnostic report is completed, the key IPP sets are attached to the diagnostic report and both the diagnostic report and the key IPP sets are stored on a Hospital Information Server (HIS) 141 which serves as the Hospital's central repository for patient data and medical history. The HIS 141 is connected to the reporting station 131 via low-speed network 112 and to the PACS server 102 via direct connection. The HIS 141 is also connected to the low-speed network 151 that serves departments in the hospital that are not connected to the high-speed network 111. User terminals 161 in those departments are connected to low-speed network 151 and provide access to the HIS 141.

When a department in the hospital needs to review a diagnostic report, the requesting department submits a request for the report from a user terminal 161 to the HIS 141 via network 115 and the report is transmitted to the user terminal 161 from the HIS 141 via network 151 along with the key IPP sets attached to the diagnostic report. In the course of reviewing the diagnostic report, a user at a user terminal 161 may want to view one or more of the key diagnostic images that formed the basis of the diagnosis. In order to view an image, the user will select the IPP set attached to the report, which is associated with the desired image, and the IPP set for that image is transmitted to data processing server 103 via network 151.

Data processing server 103 is a high-speed data processing device that is also connected to the PACS server network (i.e., high-speed network 111). The high-speed data processing server 103 is capable of performing all of the image-processing operations that are performed by the diagnostic specialists at the image display workstations 121. The data processing server 103 reads the IPP set received from user terminal 161. As previously noted, the IPP set contains parameters which specify the unprocessed image data and the image processing operations that were used to create the key diagnostic image, the data processing server 103 uses the parameters in the IPP set to retrieve the unprocessed image data and reconstruct the key diagnostic image, so that image processing of two-dimensional, three-dimensional and four-dimensional images is realized based on the image processing parameters, and the resulting image data is sent to user terminals 161 via the network 151. The high-resolution image data sent from the data processing server 103 is displayed together with the image diagnosis report on user terminal 161. Because all of the high volume data processing associated with the image processing is performed on the high-speed PACS server network, and only selected key diagnostic images are transmitted over user network 151, the increase in data traffic on network 151 will be minimized. In order to further minimize traffic loading on the low bandwidth network 151, the image data sent to user terminals 161 from the data processing server 103 may be compressed before transmission and decompressed at user terminal 161 upon arrival.

In another embodiment of the invention, users at user terminals 161 may have the ability to modify the IPP sets attached to the diagnostic reports in order to create custom diagnostic images. For example, a user may want to view only a portion of a key diagnostic image or to view the image from a different angle. In this embodiment, the user is provided with a tool set that allows the user to specify the desired image changes. The tool set makes the required changes to the IPP set before the IPP set is transmitted to the data processing server 103. These changes may be performed in an iterative fashion. That is, a user may view an image, modify the IPP set to retrieve a modified image, make another modification and retrieve another modified image, and so on. Modified IPP sets may be stored at the PACS server 102 or the HIS server 141 for subsequent retrieval and image reconstruction.

In another embodiment, instead of attaching IPP sets to the diagnostic reports, identifiers of IPP sets are attached, and image processing parameters corresponding to these identifiers are stored at a PACS server 102 or HIS server 141. In this embodiment, users at user terminals 161 who receive diagnostic reports can request a key diagnostic image by transmitting the IPP identifier to the location where the IPP set is stored. The IPP set is then sent from its storage location, which may be the PACS server 102 or the HIS server 141, to the data processing server 103 where the key diagnostic image is reconstructed as previously described.

In another embodiment, the diagnostic specialists who create the diagnostic images and diagnostic reports have access to the HIS server 141 via network 112 and have the capability to access the information stored on the HIS server 141 to supplement the diagnosis. For example, the results of image examinations from different times or different imaging modalities may be viewed by retrieving the unprocessed image data from those examinations, or the IPP sets created from processing those images may be retrieved to reconstruct the diagnostic images from those examinations. Similarly, patient medical history files may be retrieved for viewing and/or incorporation into the report. The supplemental images and data used in this manner can be referenced in the diagnostic report as key information and can be made available to users at user terminals 161 by attaching IPP sets and/or identifiers for the diagnostic images and other identifiers for the retrieval of patient information. Users may retrieve the supplemental images and/or key supplemental information by sending the IPP sets and/or identifiers to the data processing server 103 or the HIS server 141.

Figure 3:
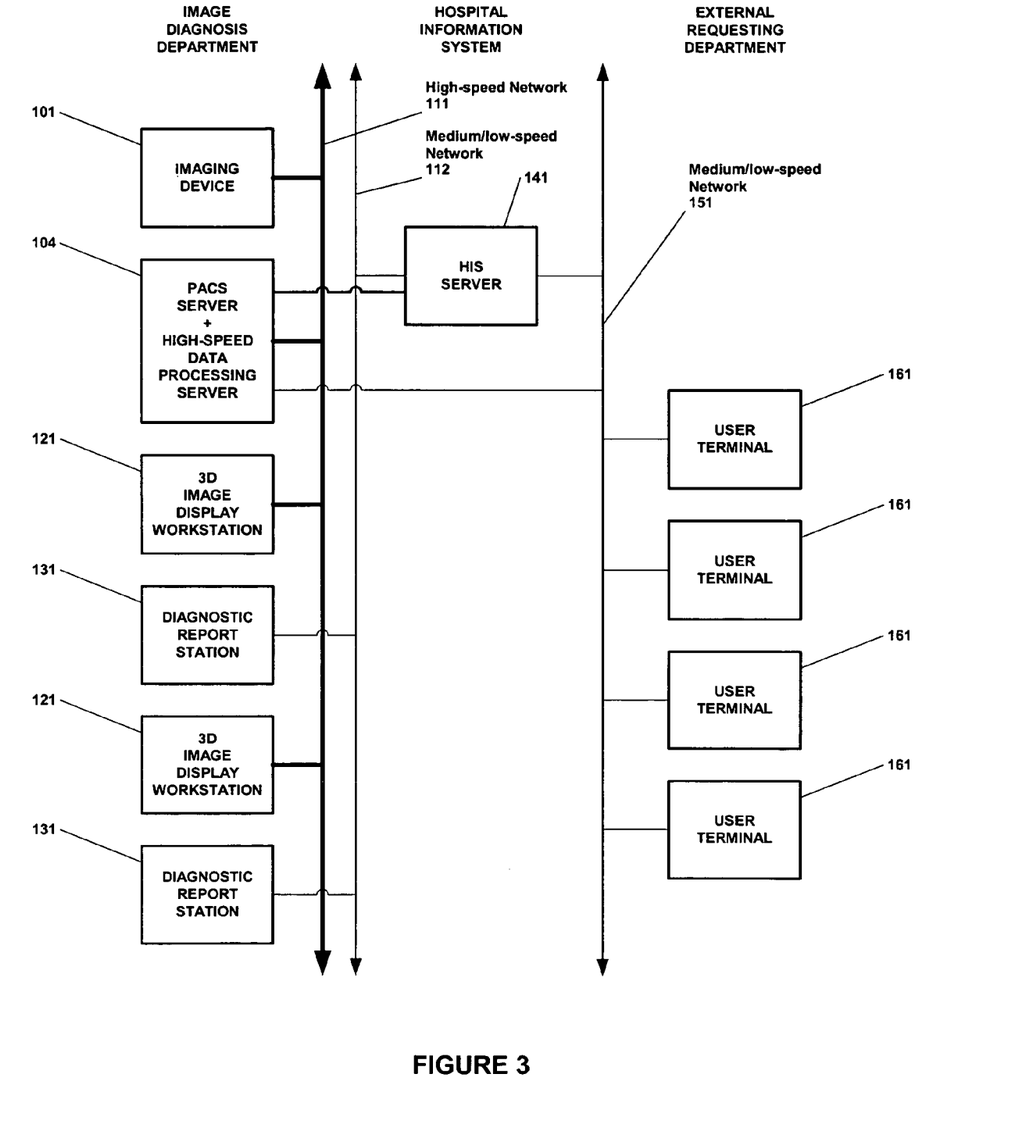
FIG. 3 is a block diagram of a system to create and disseminate diagnostic reports with medical images and other medical information in a network environment according to another embodiment of the invention.

As shown in FIG. 3, the PACS server 102 and the data processing server 103 may be integrated into a combined PACS server and data processing server (integrated server) 104. Integrating the imaging archiving function of the PACS server with the image processing function of the data processing server reduces the load on high-speed network 111 and frees resources for the creation of diagnostic images. In addition, because the data processing server, embodied separately or integrated with the PACS server function, has all of the image processing power of the image display workstations 121, the workstations may be replaced with personal computers or other terminal devices with low image processing capability where the personal computers, for example, merely transmit control signals to the data processing server and receive and display the images created on the data processing server. In another embodiment, the functionality of the diagnostic report stations 131 may be integrated with the functionality of the image display workstations, either as image processing workstations or as terminal devices with image display capability. The invention thus makes it possible to save on equipment costs and to reduce the space requirements for the system. The costs of the equipment can be reduced when a high-speed network is used together with a plurality of personal computers instead of using multiple workstations for the processing of diagnostic images.

Figure 4:
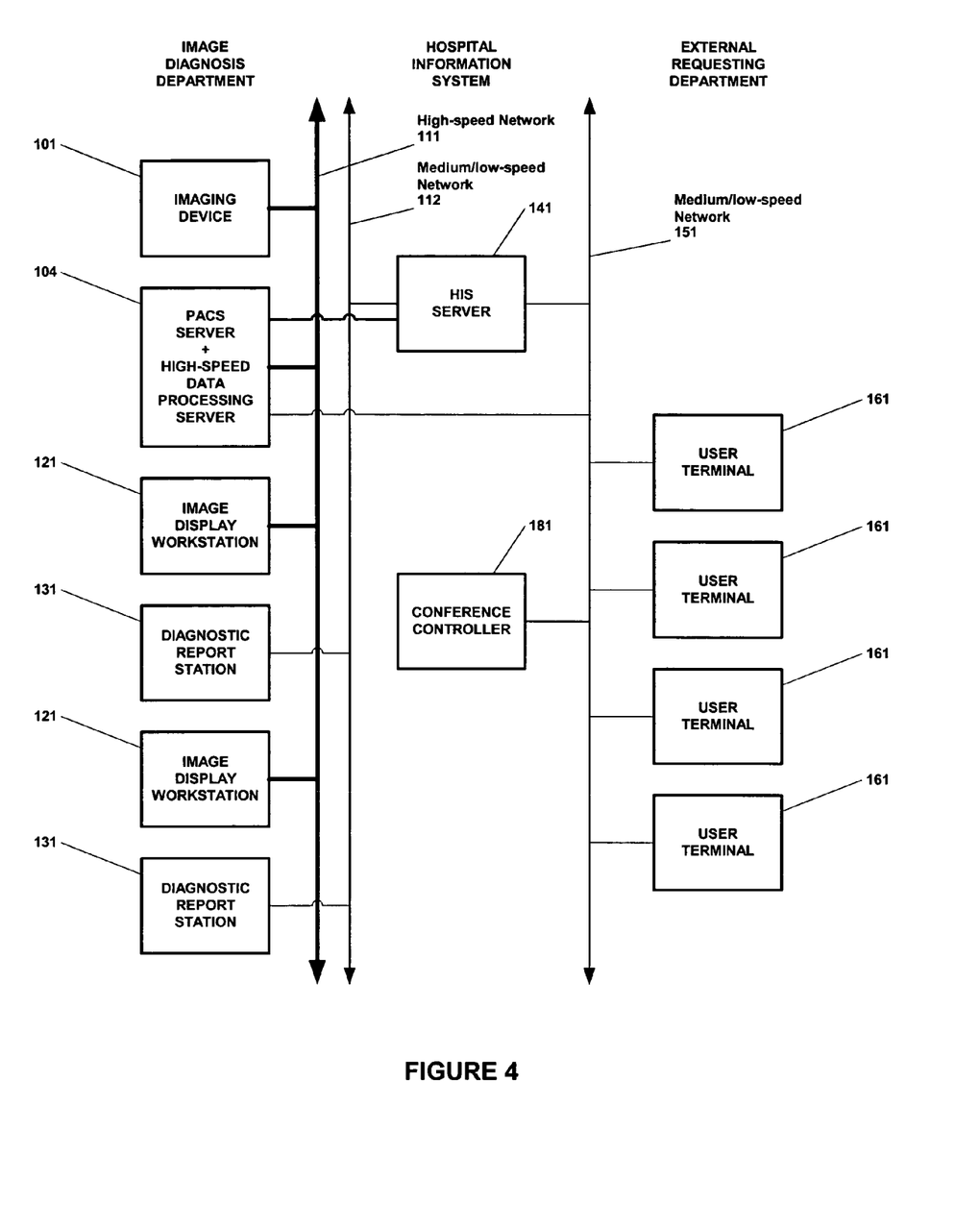
FIG. 4 is a block diagram of a system to create diagnostic reports with medical images and other medical information in a network environment according to another embodiment of the invention.

FIG. 4 shows an embodiment of the invention in which multiple users can hold a conference using image diagnosis reports. In this embodiment, a conference controller 181 is a controller, for example, of an interactive conference system or of a TV conference system that can be used by a plurality of participants. The conference controller 181 is used to schedule and manage diagnostic conferences where diagnosticians who create diagnostic reports and users of the diagnostic reports in other departments can interactively view, review and discuss and/or modify the diagnostic reports, key images and other key information. In other respects, the flow of information and data during the conference is as previously described with the exception that the information and data is distributed to multiple users.

Figure 5:
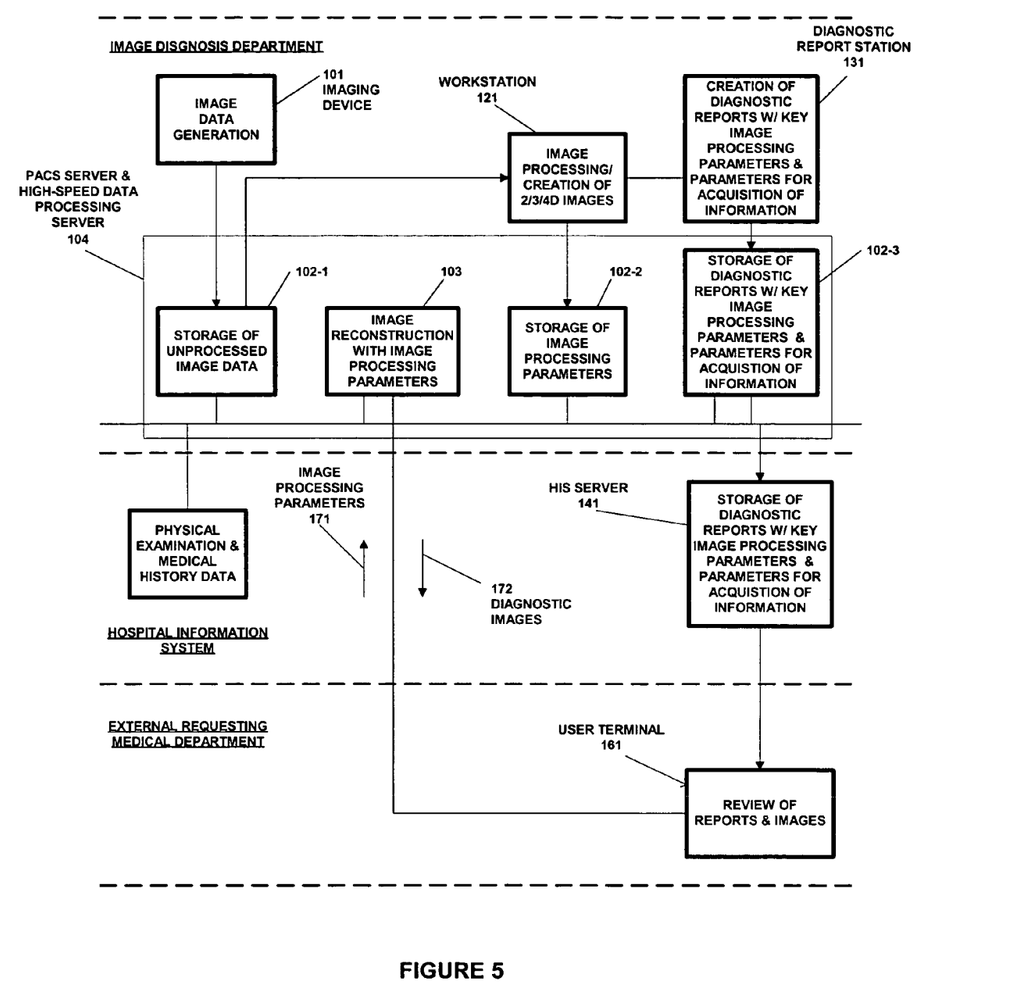
FIG. 5 is a functional block diagram of a system to create diagnostic reports with medical images and other medical information according to an embodiment of the invention.

FIG. 5 shows an architecture of a system to create medical image reports and utilize medical image data according to the present invention. Image data created with an imaging device 101 is sent to a PACS server 102-1 where it is stored. Doctors specializing in image diagnosis use workstations 121 for image processing operations to perform two-dimensional image processing and create three-dimensional and four-dimensional images. Based on the diagnostic findings, image diagnosis reports are created by using a diagnostic report station 131, which is used to create diagnostic reports. The image processing parameters used for the processing of two-dimensional images to create three-dimensional and four-dimensional images are stored at the PACS server 102-2. In order to regenerate key images that enhance the understanding of doctors at requesting medical departments, image processing parameters associated with key diagnostic images are attached to the image diagnosis report. The created image diagnosis reports and the image processing parameters attached to these reports are stored at an HIS server 141 and transmitted via a network to a user terminal 161 in a requesting department.

The transmitted image diagnosis reports can be reviewed by doctors at requesting medical departments at user terminals 161. Image processing parameters 171 are sent via a network to a data processing server 103 to create key images by clicking on an icon of an image in the image diagnosis report. Based on the image processing parameters received by the data processing server, required image data is acquired from a PACS server 102-1. Based on the image processing parameters, two-dimensional, three-dimensional and four-dimensional image processing is performed for this image data and the resulting images 172 are sent to a user terminal 161. While doctors at requesting departments observe these images at the user terminal, they can modify the image processing parameters and the data can then be transmitted again to a data server. The data server performs image processing on the basis of the modified image processing parameters, and the results are sent back to the user terminal. These operations can thus be repeated in an interactive manner. Diagnostic image data 172 can be compressed before it is transmitted to user terminal 161, where it is subsequently decompressed for viewing. In this manner, even low-speed networks can be used to support iterative image processing and viewing.

In another embodiment, in an image diagnosis report displayed on the screen of a user terminal, images transmitted from a data processing server are displayed with region and image processing parameters that can be modified in an interactive manner with a controller provided with this embodiment, which can be used even when no special software has been installed.

In another embodiment, images transmitted from a data processing server are displayed in a separate window of a diagnostic report.

In another embodiment, thumbnail images are attached to image diagnosis reports so that by clicking on these thumbnail images, a user interface is displayed on the screen for modification of image processing parameters that can be sent to a data processing server.

Although the present invention has been described with reference to specific exemplary embodiments, it will be evident that various changes and modifications made be made to these embodiments without departing from the broader spirit and scope of the invention as set forth in the claims. Accordingly, the specification and drawings are to be regarded in an illustrative sense rather than a restrictive sense.

What is claimed is:

1. A method comprising:
storing medical image data generated during a first image examination;
processing the medical image data in a sequence of image processing operations to produce a processed image;
recording the sequence of image processing operations as a sequence of image processing parameters;
storing the sequence of image processing parameters in a data file in a data storage device;
sending an image diagnosis report with the data file or an identifier of the data file to a user terminal device, the image diagnosis report including key information referencing patient medical history information and further including key information referencing results of another image examination or a different imaging modality than the first image examination;
providing a tool set to allow a user of the user terminal to input image change specification;
the tool set making changes to the sequence of image processing parameters in response to the image change specification;
in response to an input by the user of the user terminal, extracting the sequence of image processing parameters from the data file;
sending the sequence of image processing parameters to an image processor;
repeating the sequence of image processing operations on the image data, to reconstruct the processed image;
sending the reconstructed processed image to the user terminal device for display by the user terminal; and
providing a conference controller to allow the user to schedule and hold a diagnostic conference with a second user, wherein the user and the second user are allowed to interactively view and modify the diagnostic report and the key information during the diagnostic conference.

2. The method of claim 1, further comprising:
modifying the sequence of image processing operations at the terminal device; and
creating a modified processed image by performing the modified sequence of image processing operations at the image processor.

3. The method of claim 1, further comprising compressing the processed image at the image processing device and uncompressing the processed image at the terminal device.

4. The method of claim 1, wherein
storing the sequence of image processing operations in a data file further comprises storing a sequence identifier;
sending the data file to the terminal device comprises sending the sequence identifier; and
sending the sequence of image processing operations to an image processor comprises sending the sequence identifier from the terminal device to the data storage device and sending the sequence of image processing operations from the data storage device to the image processor.

5. A system comprising:
an image archiving device to store a plurality of unprocessed image data, the image archiving device connected to a first data network;
a data processor connected to the first data network, the data processor to process the plurality of unprocessed image data;
a user terminal including an image display device connected to the first data network, the image display device to display an image diagnosis report resulting from a first medical image examination, the plurality of unprocessed image data and a plurality of processed image data;
a report preparation device connected to a second data network, to generate a plurality of image diagnosis reports including said image diagnosis report, the plurality of image diagnosis reports having associated therewith a plurality of image processing parameters, wherein the plurality of image processing parameters provide instructions to the data processor to reconstruct the plurality of processed images, said image diagnosis report including key information referencing patient medical history information and further including key information referencing results of another image examination or a different imaging modality than the first image examination, wherein selection by a user of the user terminal of an item of said key information causes information referenced by said item to be transmitted to, and output by, the user terminal;
a data storage device connected to the second data network and the data processor, to store the plurality of image diagnosis reports;
a tool set to allow the user to input image change specification and to change the plurality of image processing parameters in response to the image change specification; and
a conference controller to allow the user to schedule and hold a diagnostic conference with a second user, wherein the user and the second user are allowed to interactively view and modify the diagnostic report and the key information during the diagnostic conference.

6. The system of claim 5, wherein the image display device comprises an image processor, the image processor adapted to process the plurality of unprocessed image data and to generate the plurality of image processing parameters.

7. The system of claim 5, further comprising:
a third data network connected to the data storage device, the data processor and a plurality of terminal devices, the plurality of terminal devices adapted to receive and display the plurality of image diagnosis reports, wherein the plurality of image processing parameters is extracted from the plurality of image processing reports and sent to the data processor via the third data network.

8. The system of claim 5, wherein the image archiving device and the data processor are integrated.

9. The system of claim 5, wherein the image display device and the report preparation device are integrated.

10. The system of claim 5, wherein the first data network is a high-speed network.

11. The system of claim 7, wherein the data processor reconstructs the plurality of processed images and transmits the plurality of processed images to the plurality of terminal devices.

12. The system of claim 7, wherein at least one of the second data network and the third data network is low-speed network.

13. The system of claim 7, wherein at least one of the second data network and the third data network is a medium-speed network.

14. The system of claim 10, wherein the plurality of processed images is compressed at the data processor and decompressed at the plurality of terminal devices.

15. A system comprising:
- a picture archiving and communications system (PACS) server to store a plurality of unprocessed medical image data, the PACS connected to a PACS server network;
- a data processing server to perform image processing of the plurality of unprocessed medical image data in a sequence of image processing operations, the sequence of operations defined by an image processing parameter (IPP) set, the data processing server connected to the PACS server network;
- a report preparation station connected to the PACS server, to prepare a plurality of image diagnosis reports, wherein the plurality of image diagnosis reports comprise a plurality of image diagnoses and a plurality of image processing parameter (IPP) sets to recreate a plurality of key diagnostic images, wherein the plurality of image diagnosis reports further comprise key information referencing patient medical history information and further including key information referencing results of other image examinations or other imaging modalities;
- an information server to store the plurality of image diagnostic reports, the information server connected to the PACS server;
- a user terminal including a display device, connected to the information server and the data processing server, to display the plurality of image diagnostic reports, to send the plurality of IPP sets to the data processing server, to receive the plurality of key diagnostic images from the data processing server and to display the plurality of key diagnostic images;
- a tool set to allow a user to input image change specification and to change the plurality of IPP sets in response to the image change specification; and
- a conference controller to allow the user to schedule and hold a diagnostic conference with a second user, wherein the user and the second user are allowed to interactively view and modify the diagnostic report and the key information during the diagnostic conference.

16. The system of claim 15, wherein the plurality of image diagnosis reports further comprises:
- a plurality of IPP set identifiers to retrieve IPP sets from the information server; and
- a plurality of additional information parameters to retrieve additional information from the information server.

17. The system of claim 15, wherein the plurality of IPP sets maybe modified at the terminal display device and transmitted to the data processor, wherein the data processor creates a plurality of modified images.

18. The system of claim 15, wherein the PACS server is integrated with the data processing server.

19. The system of claim 15, wherein the image display device and the report preparation device are integrated.

20. The system of claim 15, wherein the plurality of key diagnostic images is compressed before it is sent from the data processing server to the terminal display device and decompressed at the terminal display device.

21. The system of claim 15, wherein the terminal display device represents the plurality of IPP sets as a plurality of thumbnail images of the plurality of key diagnostic images.

22. The system of claim 21, wherein selecting the plurality of thumbnail images of key diagnostic images causes the plurality of IPP sets to be sent to the data processing server.

23. The system of claim 21, wherein the plurality of thumbnail images is linked to a user interface that is adapted to modify the plurality of IIPP sets attached to the diagnostic report.

24. A system comprising:
- means for viewing an image diagnosis report simultaneously at a plurality of terminal display devices, the report having a plurality of image processing parameter sets representing key images generated from an image examination, the report including key information referencing patient medical history information and further including key information referencing results of another image examination or a different imaging modality than said image examination;
- means for modifying an image processing parameter set for a key image while the key image is being viewed, wherein the means for modifying the image processing parameter set includes a tool set to allow a user of the means for viewing the image diagnosis report to input image change specification and to make changes to the image processing parameter set in response to the image change specification;
- means for transmitting a modified image processing parameter set to a data processing server, wherein the modified image processing parameter set modifies the image processing used to create the key image and creates a modified key image from an unprocessed image data set;
- means for transmitting the modified key image to the plurality of terminal display devices;
- means for displaying the modified key image simultaneously at the plurality of terminal display devices;
- means for communicating and exchanging information among the plurality of terminal display devices; and
- a conference controller to allow the user to schedule and hold a diagnostic conference with a second user, wherein the user and the second user are allowed to interactively view and modify the diagnostic report and the key information during the diagnostic conference.

25. The method of claim 1, further comprising:
- receiving a selection by the user of the user terminal of an item of said key information; and
- in response to the selection, causing information referenced by said item to be transmitted to, and output by, the user terminal.

26. The system of claim 15, wherein selection by a user of the user terminal of an item of said key information causes information referenced by said item to be transmitted to, and output by, the user terminal.

* * * * *